(12) United States Patent
Little

(10) Patent No.: US 6,624,897 B1
(45) Date of Patent: Sep. 23, 2003

(54) APPARATUS AND METHOD FOR FEATURE EDGE DETECTION IN SEMICONDUCTOR PROCESSING

(75) Inventor: Joseph R. Little, Caldwell, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/292,396

(22) Filed: Apr. 15, 1999

(51) Int. Cl.⁷ .............................................. G01B 11/14
(52) U.S. Cl. ........................ 356/614; 356/615; 356/630
(58) Field of Search ................................ 356/614, 615, 356/630, 375

(56) References Cited

U.S. PATENT DOCUMENTS

| | | |
|---|---|---|
| 4,631,416 A | 12/1986 | Trutna, Jr. |
| 4,991,962 A | 2/1991 | Jain |
| 5,343,292 A | 8/1994 | Brueck et al. |
| 5,726,074 A | 3/1998 | Yabe |
| 5,978,074 A * | 11/1999 | Opsal et al. .................. 356/72 |
| 6,278,519 B1 * | 8/2001 | Rosencwaig et al. ....... 356/369 |

* cited by examiner

*Primary Examiner*—Frank G. Font
*Assistant Examiner*—Roy M. Punnoose
(74) *Attorney, Agent, or Firm*—Dickstein Shapiro Morin & Oshinsky LLP

(57) ABSTRACT

A method and apparatus is provided to identify material boundaries and assist in the alignment of pattern masks in semiconductor fabrication. The invention probes a layer step or feature edge of an individual wafer using spectroscopic reflectance to detect a change in the reflectance spectral response. In integrated circuit fabrication, a wafer is subjected to wafer fabrication processes to produce a number of individual layers on a semiconductor substrate. During processing a reflectometer, a light emitting and collecting device, emits a specific range of electromagnetic wavelengths which are reflected from the wafer surface. The intensity of the reflected light is monitored for changes which signify the detection of a feature edge. The use of a specific range of electromagnetic wavelengths with the reflectometer allows the apparatus to detect feature edges covered by visibly-opaque material. After a feature edge has been detected, positional information associated with the detected feature edge may be used to accurately align a pattern mask.

31 Claims, 11 Drawing Sheets

APPARATUS AND METHOD FOR FEATURE EDGE DETECTION IN SEMICONDUCTOR PROCESSING

BACKGROUND OF THE INVENTION

1. Field of the Invention

This invention relates to semiconductor processing and, in particular, to a method and apparatus for improving the alignment of pattern masks to semiconductor wafers.

2. Description of the Related Art

Trends toward smaller critical dimensions in semiconductor processing have caused an exponential increase in the precision with which fabrication processes must be performed by the semiconductor device manufacturer. Semiconductor based integrated circuits are typically manufactured through the formation of a set of layers on a wafer containing many integrated circuit areas which will later be separated into individual dies. Very thin layers of material are deposited one on top of the other in patterns to form integrated circuit components. One technique of deposition and patterning is photolithography wherein a material layer is first coated with a light-sensitive photoresist. The photoresist is exposed through a pattern mask of a desired circuit pattern. The exposed photoresist is developed to remove, depending upon the type of photoresist used, either the exposed or unexposed resist. Etching and/or deposition processes are then used to create the desired circuit within the pattern created.

It is imperative to the process of photolithography that the pattern mask be precisely aligned on a wafer during processing. The overlay of the mask, the measure of how accurately the pattern mask was aligned, will often determine whether the wafer will be functional or must be discarded. Because each wafer must undergo numerous photolithography processing steps, the alignment of each pattern mask, especially the last ones used, is dependant upon the correct alignment of earlier masks. Poor overlay destroys the intended electrical properties of a circuit device on a wafer.

Prior art alignment approaches have used numerous methods for aligning a pattern mask to a wafer. One such method is the formation or use of reflective targets within the material layers deposited on a wafer prior to the alignment of the pattern mask. The targets, such as vertical scores or pronounced feature edges between two material layers, are illuminated by a light source and the resulting contrast created by the target is used to visually align the pattern mask. However, in wafers in which, for example, an oxide layer has been deposited in a silicon substrate such that the surfaces of the oxide and the substrate are even, the system fails because no physically distinct feature edge exists. In addition, the detection of minute feature edges is further complicated after numerous material layers have been deposited on top of the feature edge which must be detected. Visibly opaque materials and variations in colors between material layers will also degrade the performance of such a system.

U.S. Pat. No. 5,343,292 (Brueck, et al.), U.S. Pat. No. 4,991,962 (Kantilal Jain), and U.S. Pat. No. 4,631,416 (William Trutna Jr.) use interferometry to establish a phase shift within reflected light to create target patterns for alignment of a mask. The phase shift of a wide light beam as it encounters a feature edge, the boundary between a substrate and a material layer which has been deposited into a substrate, can be detected if that light beam is only reflected by the substrate material. A diffraction grating pattern will emerge in the reflected light and this can be used to align pattern masks. However, the existence of material layers above the edge to be detected dilutes the precision of this measurement technique by weakening the interference pattern. In addition, interferometry systems which rely upon a physically distinct edge are imprecise when two materials have equivalent heights at the material boundary edge.

None of the described methods allows for in-line identification of feature edges to allow accurate and repeatable registration of pattern masks within the increasingly reduced critical dimensions made possible by recent advancements in wafer fabrication.

SUMMARY OF THE INVENTION

The present invention provides a method and apparatus that is able to overcome some of the problems attendant the alignment of pattern masks in semiconductor fabrication of small critical dimension devices.

The above and other features and advantages of the invention are achieved by providing an apparatus for the detection of a layer step or feature edge of a die or wafer using spectroscopic reflectance to detect a change in the reflectance spectral response at the step or edge. The detection of a feature edge may be used, for example, to align a pattern mask for photolithography processing of the wafer.

In integrated circuit fabrication, a wafer is subjected to wafer fabrication processes to produce a number of individual layers on a semiconductor substrate. During processing, a reflectometer emits electromagnetic radiation having a predetermined wavelength range. The intensity or reflectivity of the radiation which is reflected from the wafer is monitored for changes which signal the detection of a feature edge within or on the wafer. The use of a specific range of electromagnetic wavelengths with the reflectometer allows the apparatus to detect feature edges covered by material which is visibly opaque, that is the material is opaque or semi-opaque in the visible wavelength range of 400 nm to 700 nm. After a feature edge has been detected, the apparatus may be used to accurately align a pattern mask according to the data collected by the reflectometer.

The above and other advantages and features of the present invention will be better understood from the following detailed description of the preferred embodiment which is provided in connection with the accompanying drawings.

DETAILED DESCRIPTION OF PREFERRED EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized, and that structural, logical and electrical changes may be made without departing from the spirit and scope of the present invention. Wherever possible, like numerals are used to refer to like elements and functions in the various figures of the drawings and between the different embodiments of the present invention.

Figure 1:
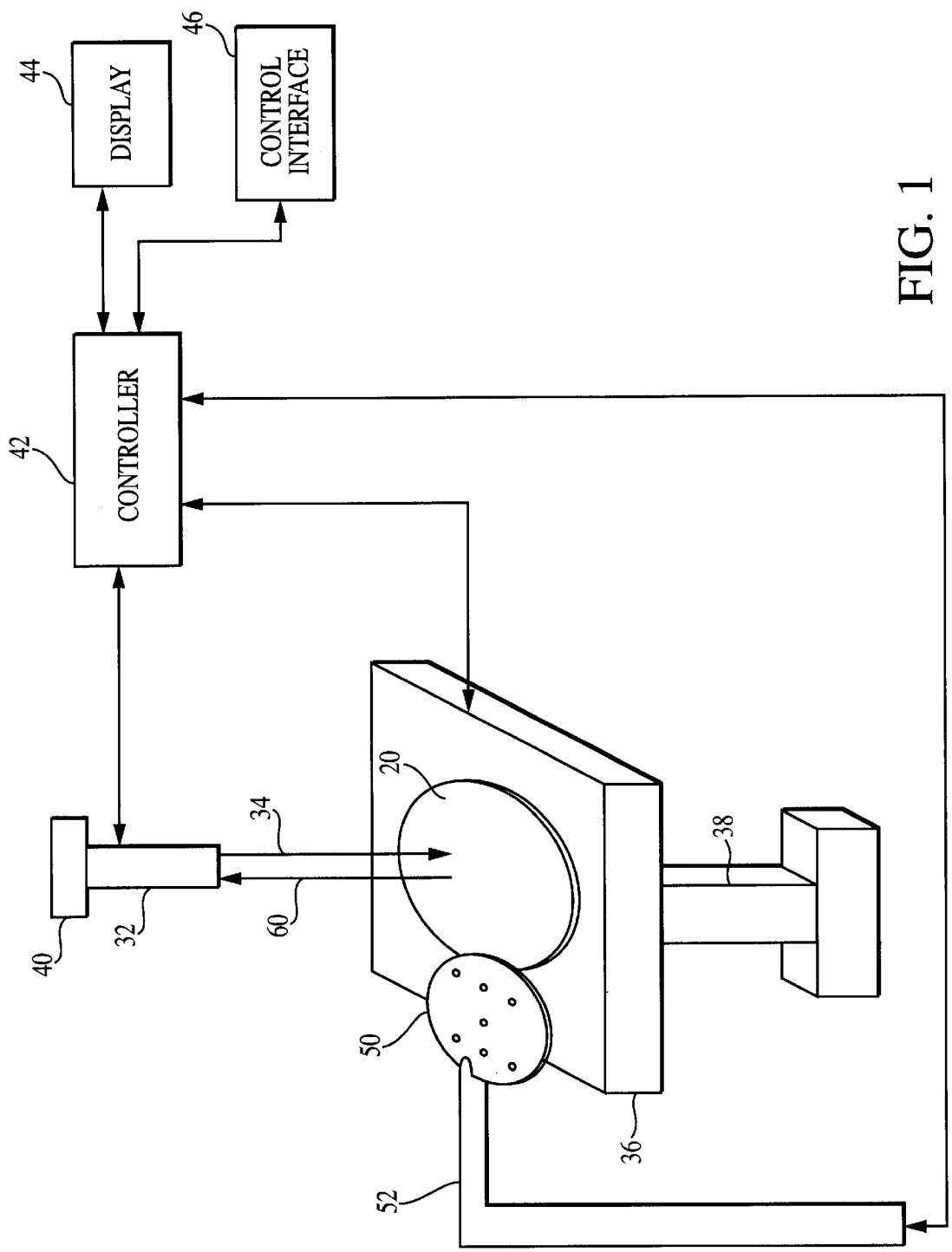
FIG. 1 is a perspective view of a preferred embodiment of the present invention.

A feature edge detection system in accordance with the present invention is illustrated generally in FIG. 1. The detection system is part of an automated wafer fabrication system for processing a wafer 20. The wafer 20 is mounted for processing on a coordinate table 36 attached to a base 38 capable of three dimensional movement along the X, Y, and Z axis, preferably at least along the plane of the surface of the wafer 20 which is to be processed. An element 52, preferably a robotically controlled element, grips pattern mask 50, and is capable of moving pattern mask 50 in response to control signals from the controller 42. Reflectometer 32 produces a radiation incident beam 34 which intersects with a surface of the wafer, preferably at an angle approximately perpendicular to that surface. The incident beam 34 is comprised of electromagnetic radiation having a predetermined wavelength range and may have a variable cross-sectional area depending upon the critical dimensions of the feature edge which must be detected on the wafer 20. The wavelength range of the incident beam 34 is preferably between about 100 nm to about 1000 nm. The reflected beam 60 is the reflection of incident beam 34 which is then collected in the reflectometer 32. The reflectometer exploits the material property of reflectivity to operate. Reflectivity is the property of illuminated objects, e.g. a wafer, to re-radiate or reflect a portion of the incident electromagnetic radiation energy. The reflectometer 32 measures changes in intensity or reflectivity of the reflected beam 60 relative to the intensity of the incident beam 34. As illustrated in greater detail in FIG. 2, the intensity of the reflected beam 60 will be different than the intensity of the incident beam 34 depending upon the wavelength range of the beam, the absorption coefficient of the wafer 20 layers 24, 26, 28, 30 and the substrate 22, and the distance traveled by the incident beam 34 and reflected beam 60 through the material layers 24, 26, 28, 30. The intensity of the reflected beam 60 may be measured in relative terms of intensity and/or reflectivity to a standard which may chosen by an operator.

The reflectometer 32 is attached to a mount 40 which is preferably capable of movement at least along the plane of the wafer 20. Preferably the reflectometer 32 or the coordinate table 36 is also capable of vertical or Z axis movement to allow focusing of the incident beam 34 on the surface of the wafer 20. The incident beam 34 is moved along the wafer 20 through relative movement between the coordinate table 36 and the mount 40. One is generally stationary, while the other is moveable. The movement of the coordinate table 36 or mount 40 is directed by the controller 42 (FIG. 1) responsive to information received from control interface 46. The coordinate table 36 provides support for the wafer 20 and monitors the position of the wafer 20 in relation to a fixed point or to the reflectometer 32. Coordinate table 36 is preferably a platform capable of movement along the plane of the wafer 20 and transmitting a position signal to the controller 42. The position signal is at least the x and y coordinates of the current position of the coordinate table 36 within the plane of the wafer 20 relative to a fixed point. The coordinate table 36 is comprised of motors such as, for example, DC-motors, stepping-motors, pulsed motors, or rotary hydraulic motors and may have a dedicated microprocessor or a general purpose microprocessor programmed with a mathematical coordinate table capable of monitoring the current position of the coordinate table with relation to a fixed point. Operation of the coordinate table 36 may be accomplished, for example, by control signals from the controller 42. Controller 42 is further connected to a display 44 capable of visually displaying the data from reflectometer 32 in graphical form and a control interface 46, for example a keypad, which allows an operator to control the use of the FIG. 1 detection system.

Figure 2:
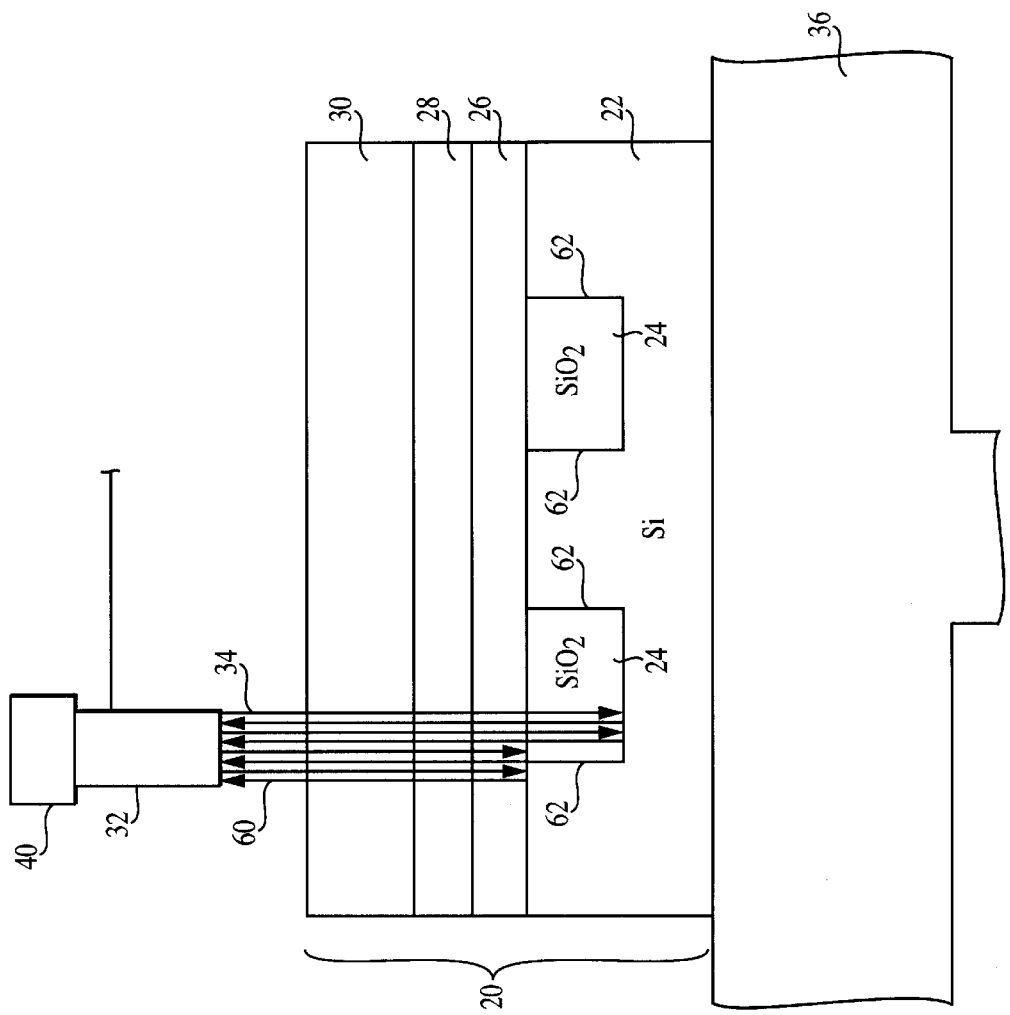
FIG. 2 is a perspective view of a wafer used to illustrate a preferred embodiment of the present invention.

FIG. 2 shows in an enlarged fashion a portion of the FIG. 1 detection system when in use. The wafer 20 at the illustrated stage of processing includes a plurality of material layers 22, 24, 26, 28, 30. For example, a semiconductor substrate 22 is processed such that an oxide layer 24 is formed therein and visibly-opaque material layers 26, 28, 30 are formed in series over the substrate 22 containing the oxide layer 24. Feature edges 62 are formed at the boundary between the substrate 22 and the oxide layer 24. The substrate 22 of the wafer 20 may be any material suitable for use as a substrate for integrated circuit devices which are reflective in the usable spectrum (150 nm to 1100 nm wavelengths), preferably silicon (Si) or gallium arsenide (GaAs). Visibly-opaque material layers 26, 28, 30 may be any visibly-opaque material used in the processing of integrated circuits such as, for example, polyimide, polysilicon, Wsix, Nitride, oxide or other resist coatings. Thin layers of metallization, e.g. aluminum, may also be present on the wafer 20 so long as they remain penetrable by the chosen wavelength range of electromagnetic radiation incident beam 34 being used. For example, one or more metallization layers comprised of one or more of a group of metals including titanium, copper, aluminum, platinum, and tungsten having a thickness of less than approximately 500 Angstroms would not significantly degrade the radiation incident/reflected beams 34, 60 used in the present invention.

Preferably the beam intersects the wafer 20 perpendicular to the plane of the wafer 20. The incident beam 34, depending upon the predetermined wavelength range, will pass through visibly-opaque material layers 26, 28, 30 and oxide layer 24 to the substrate 22. The beam is reflected by the substrate 22 and reflected beam 60 and is collected in the reflectometer 32. As shown in FIG. 2, the reflectance path of reflected beam 60 is different on the left and right sides of a feature edge 62.

Figure 3:
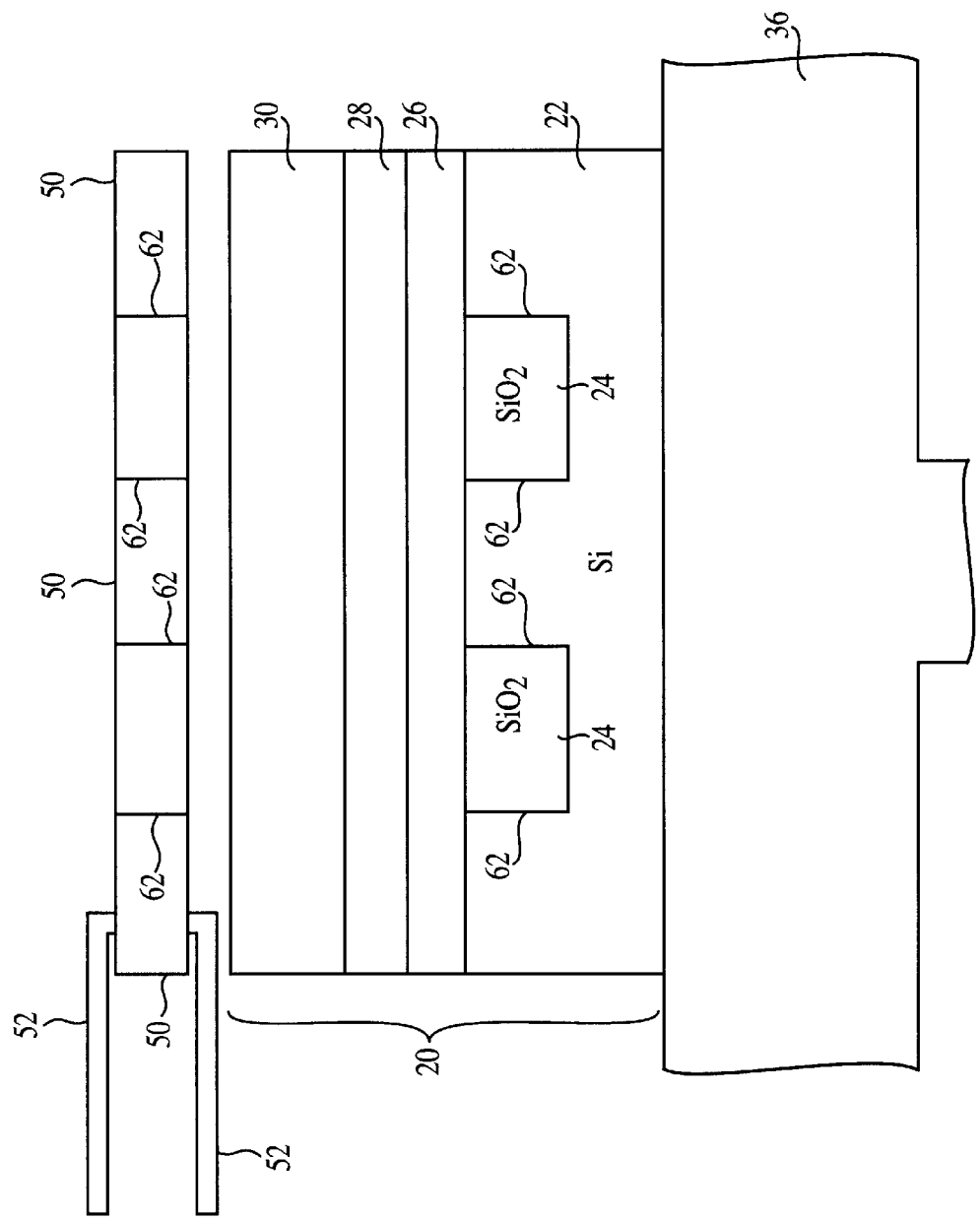
FIG. 3 is another perspective view of a wafer used to illustrate a preferred embodiment of the present invention.

FIG. 3 shows a pattern mask 50 such as is commonly used in integrated circuit manufacture which is aligned on the wafer 20 such that a feature edge 62 of the mask 50 is parallel to the feature edge 62 separating two layers of wafer 20, for example the substrate 22 and the material layer 24. An element 52 moveable in two or, preferably, three dimensions positions the mask 50 responsive to control signals from the controller 42.

The reflectometer 32 may be any device capable of producing an electromagnetic incident beam 34 of a predetermined wavelength range directed at the wafer 20 and collecting reflected beam 60 to measure the intensity or reflectivity of the reflected beam 60 over the predetermined wavelength range. The controller 42 is preferably a general use microprocessor capable of receiving input from the reflectometer 32, the control table 36, and the input interface 46. The controller 42 may be dedicated to the system 5 or may be used to control other wafer fabrication processes as well.

Figure 4:
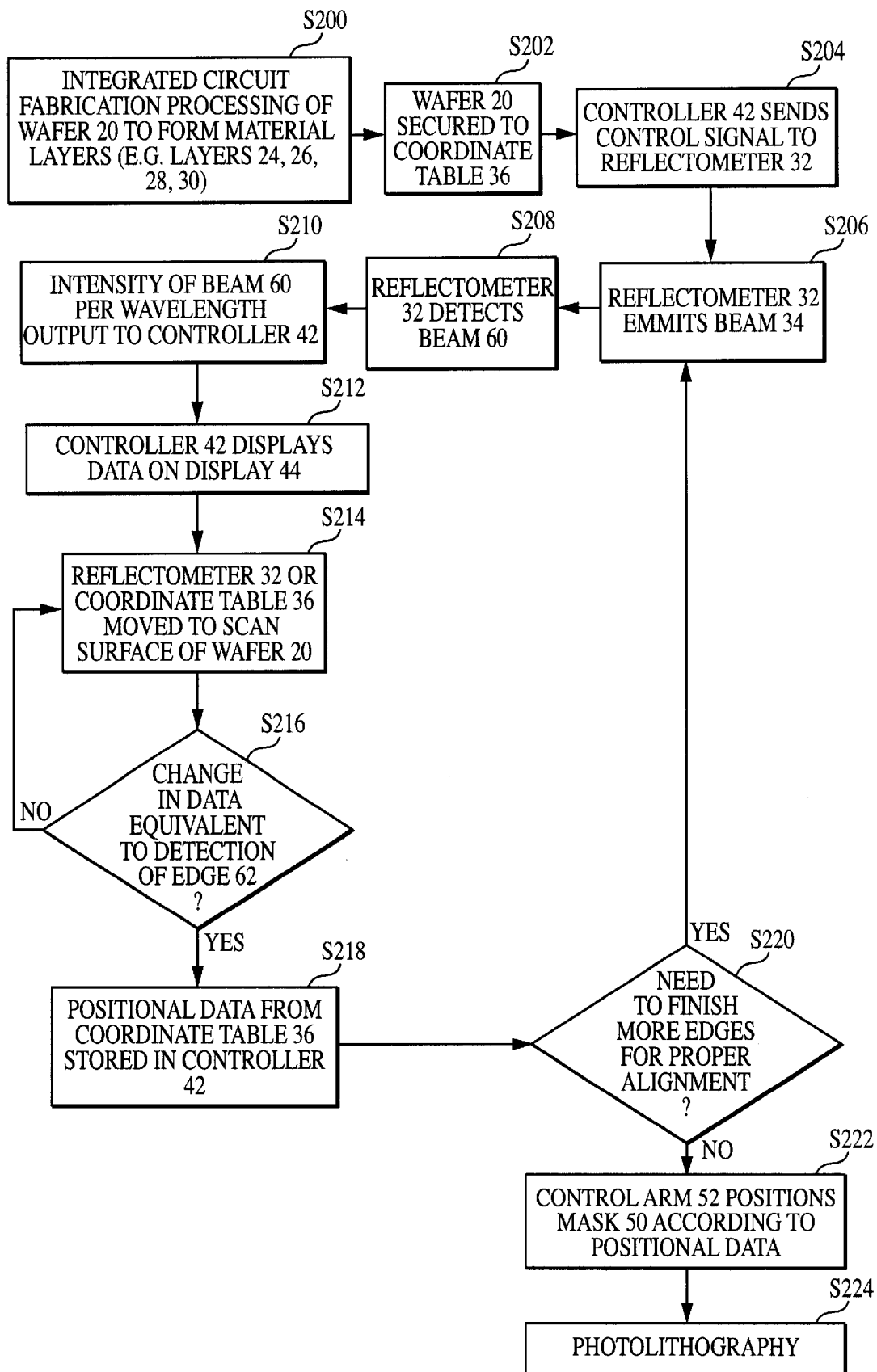
FIG. 4 is a flow chart outlining the steps of the present invention.

The process for implementing the FIG. 1 detection system to align a pattern mask 50 onto the wafer 20 will next be described with reference to FIG. 4. The wafer 20, which may ultimately be diced and yield many dies, is subjected to integrated circuit processing such that at least material layer(s) 24 are formed on and/or within the substrate 22 in step S200. This may occur through etching, deposition, prior photolithography processing, and other methods known in the art. Often, portions of the substrate 22 are removed and filled with an oxide to form material layers 24 which are substantially flush with the surface of the substrate 22. For example, a silicon substrate 22 may have silicon oxide ($SiO_2$) layers 24 which are deposited in etched portions of the substrate 22, as shown in FIGS. 2, 3. Due to the small size of the oxide layers 24 and the similarity in color between a substrate semiconductor and an oxide of that semiconductor, e.g. Si and $SiO_2$, visual or interferometric inspection of the surface of the wafer 20 can be insufficient to detect the feature edge 62 between the substrate 22 and oxide layers 24. This is especially true in the case in which several visibly-opaque material layers 26, 28, 30 have been deposited onto the wafer 20 in prior processing. Deposition of the visibly-opaque material layers 26, 28, 30 may be necessary to the processing of the wafer 20 prior to use of the mask 50.

Returning to FIG. 4, once the wafer 20 has been secured, the mask 50 must be aligned to continue processing, e.g. to complete photolithography processing, of the wafer 20. The wafer 20 is placed onto and/or secured to the coordinate table 36 in step S202. The wafer 20 may already be on the coordinate table 36 if the coordinate table 36 has been used in prior processing steps. In step S204, the controller 42 transmits control signals to the reflectometer 32 to begin emission of the incident beam 34. This step may be part of an automated process or may be initiated by an operator using control interface 46. The reflectometer 32 emits electromagnetic radiation in the form of an incident beam 34 directed towards at least one surface of the wafer 20 in step S206. The incident beam 34 preferably has a minimum spot size, e.g. less than 10 microns in area, preferably less than about 1 micron in area in the form of a rectangle or other right angled shape. The wavelength range of the incident beam 34 is chosen such that it passes through the material layers above the substrate 22 (e.g. material layers 24, 26, 28 30) and is reflected from the surface of the substrate 22 as the reflected beam 60 which is collected by the reflectometer 32 in step S208. The reflectometer 32 measures the intensity of the reflected beam 60 over the predetermined wavelength range and outputs the intensity reading to the controller 42 in step S210. The controller 42 displays the data from reflectometer 40 onto a display 44 in a form readable by an operator in step S212. One such display may be a graph of intensity versus wavelength or, alternatively, a graphical representation of the wafer 20 as reflected by the reflected beam 60. In step S214, the coordinate table 36 and, therefore, the wafer 20 are moved along the plane of the wafer 20 or, alternatively, the reflectometer 32 is moved along the plane of the wafer 20 such that the entire surface or a selected portion of the surface of the wafer 20 may be scanned.

A feature edge 62 is detected in step S216 by monitoring the signal from the reflectometer 32 for a sudden change in the intensity versus wavelength data output from reflectometer 32. If a sudden change or sharp derivation in intensity is detected, the operator or controller 42 compares the change to known data for the specific chemical composition of the substrate 22 and material layers 24, 26, 28, and 30 in step S218. If no feature edge 62 is detected of step S216, the signal from the reflectometer 32 continues to be monitored in step S214.

If the change corresponds to known data for a feature edge 62, the positional data of the feature edge 62 in relation to the wafer 20 is calculated and stored in controller 42 through the use of the coordinate table 36 in step S218. In step S220 the operator or controller 42 determines whether a sufficient number of feature edges 62, preferably a minimum of two, have been detected to allow for proper alignment of the mask 50. The feature edge detection process may be repeated in step S206 if additional feature edges 62 must be detected.

Figure 5:
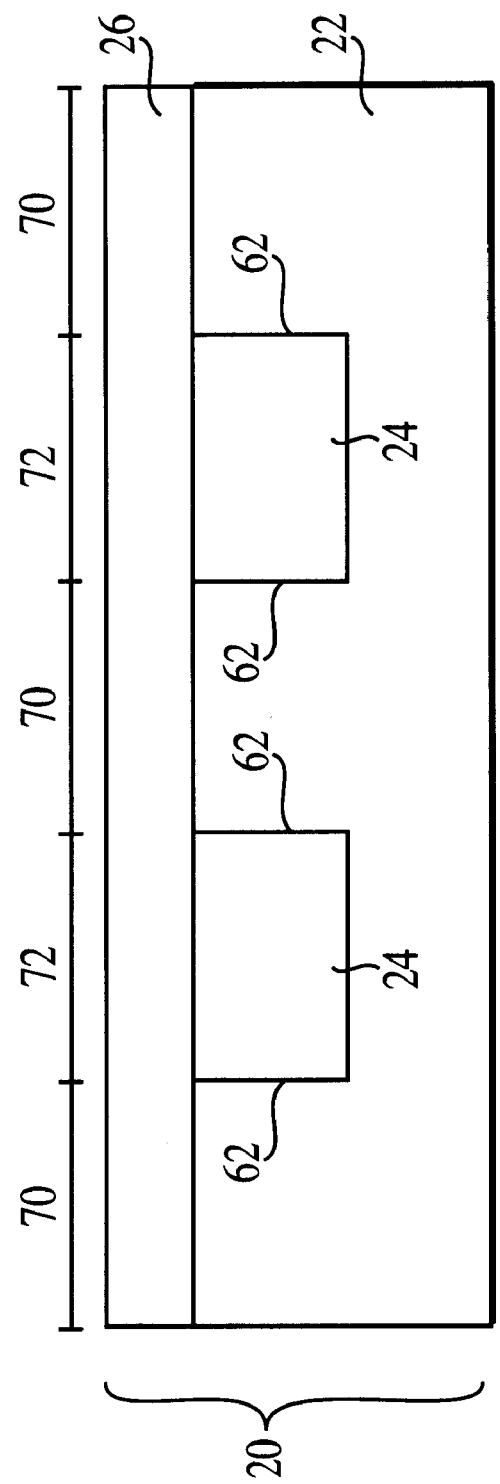
FIG. 5 is a perspective view of a wafer used to illustrate a preferred embodiment of the present invention.
Figure 6:
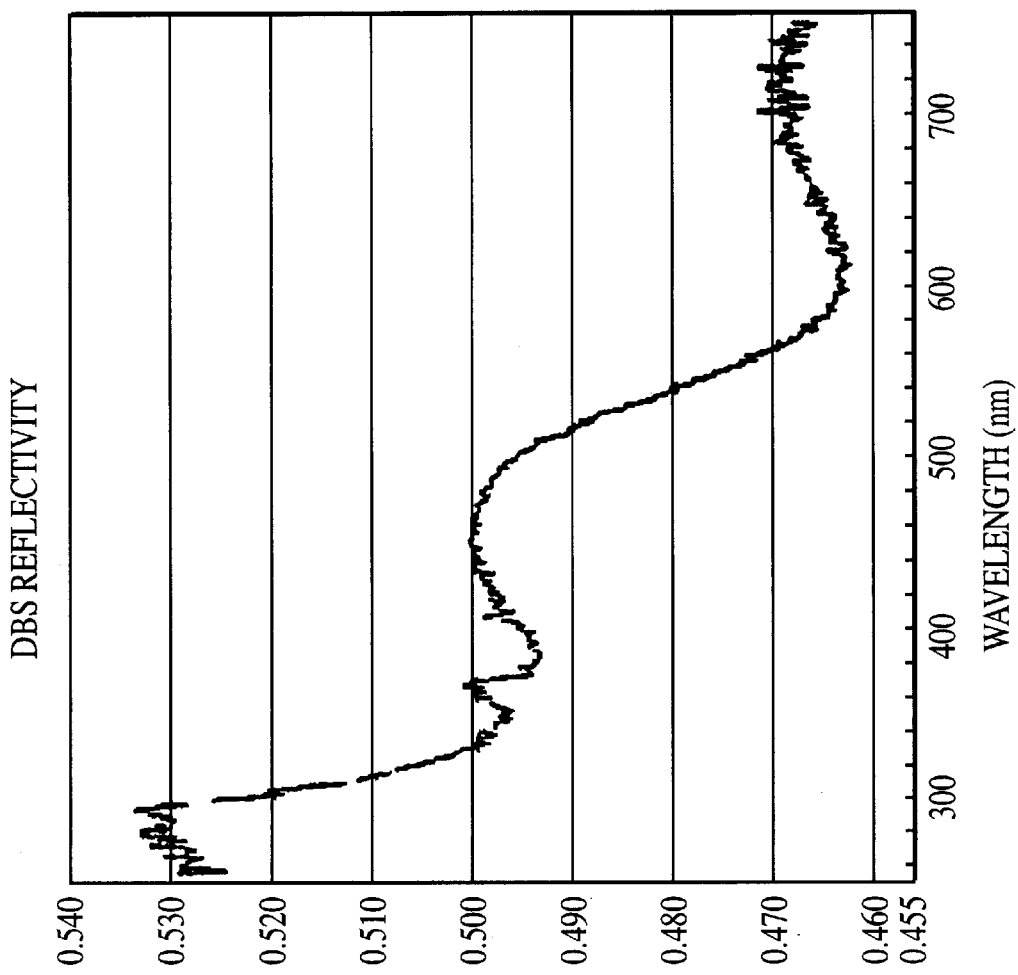
FIG. 6 is a graphical representation of reflectivity versus wavelength for the wafer of FIG. 5 measured in accordance with a preferred embodiment of the present invention.
Figure 7:
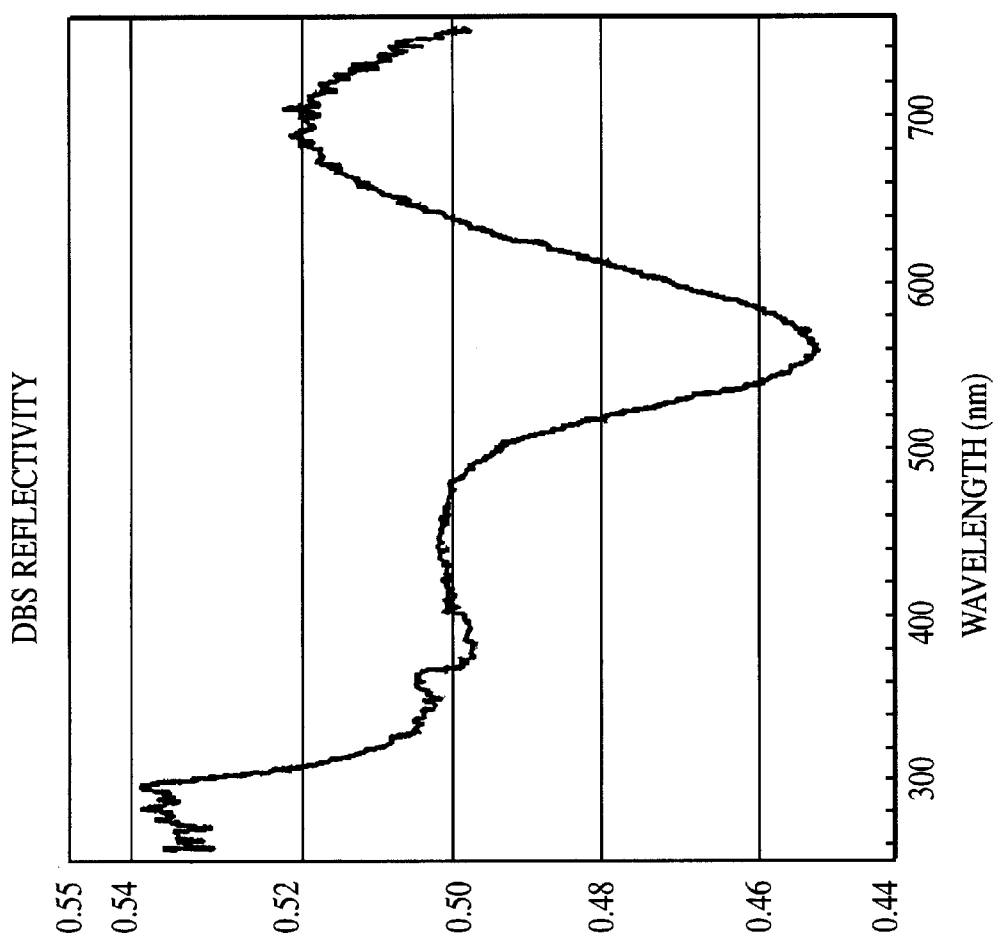
FIG. 7 is a graphical representation of reflectivity versus wavelength for the wafer of FIG. 5 measured in accordance with a preferred embodiment of the present invention.

To further illustrate detection of a feature edge 62 through analysis of the derivation of intensity patterns, FIG. 5 shows a wafer 20 comprised of a silicon substrate 22 and a variety of material layers including a silicon oxide layer 24 having a thickness of approximately 1000 Angstroms and a Wsix layer 26 having a thickness of approximately 1250 Angstroms. FIGS. 6–7 display graphical representations of reflectivity versus wavelength of the beams 34, 60 directed at and reflected from sections 70 and 72 of the wafer 20, respectively. FIG. 6 corresponds to the reflectivity pattern seen over a wavelength range of about 250 nm to about 750 nm for the sections 70 of the wafer 20 which are comprised of the silicon substrate 22 and the Wsix layer 26. As the reflectometer 32, or alternatively, the wafer 20 itself, moves in a direction parallel to the surface of the wafer 20, the graphical representation of the intensity versus the wavelength of the reflected beam 60 will change to the intensity pattern as shown in FIG. 7, as the beam moves from section 70 to section 72, the latter of which is comprised of the silicon substrate 22, silicon oxide layer 24, and Wsix layer 26. The obvious significant and sudden change in the graphical display signals the detection of a feature edge 62. In this example the feature edge corresponds to the boundary between the silicon substrate 22 and the silicon oxide layer 24.

Figure 8:
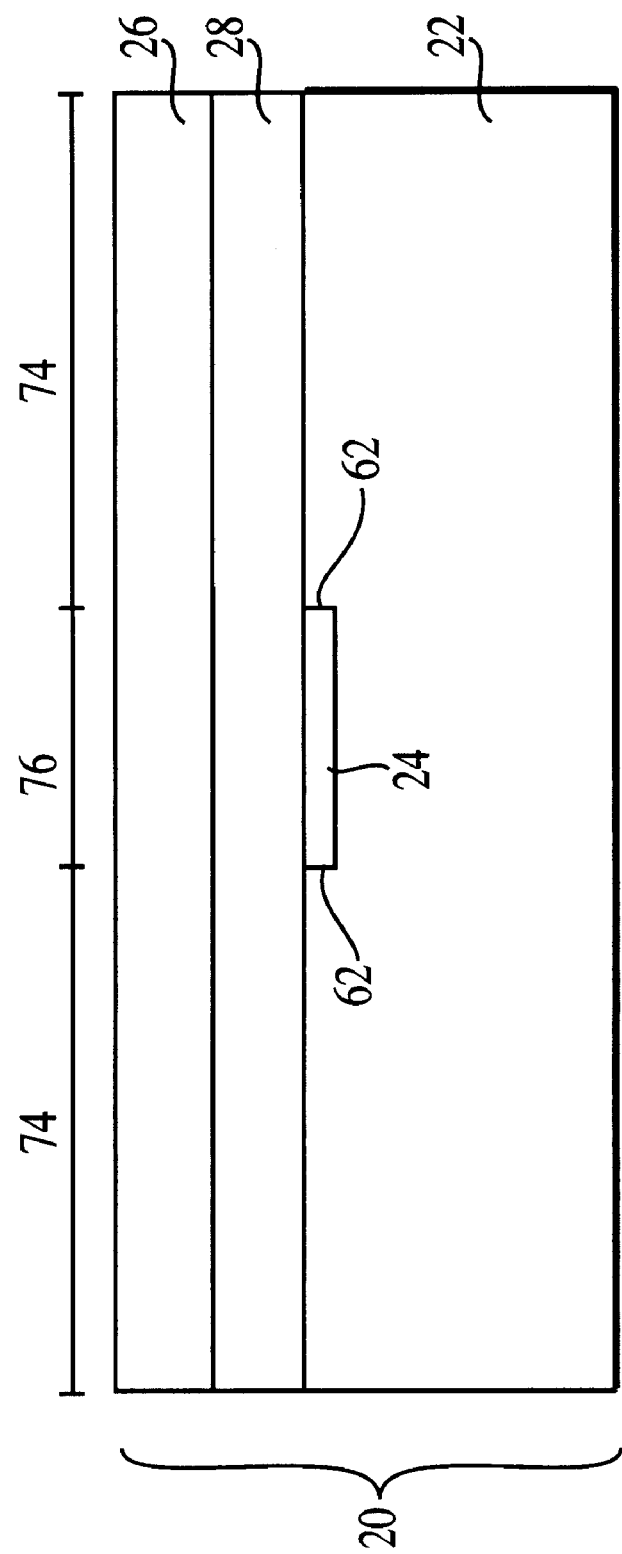
FIG. 8 is a perspective view of a wafer used to illustrate a preferred embodiment of the present invention.
Figure 9:
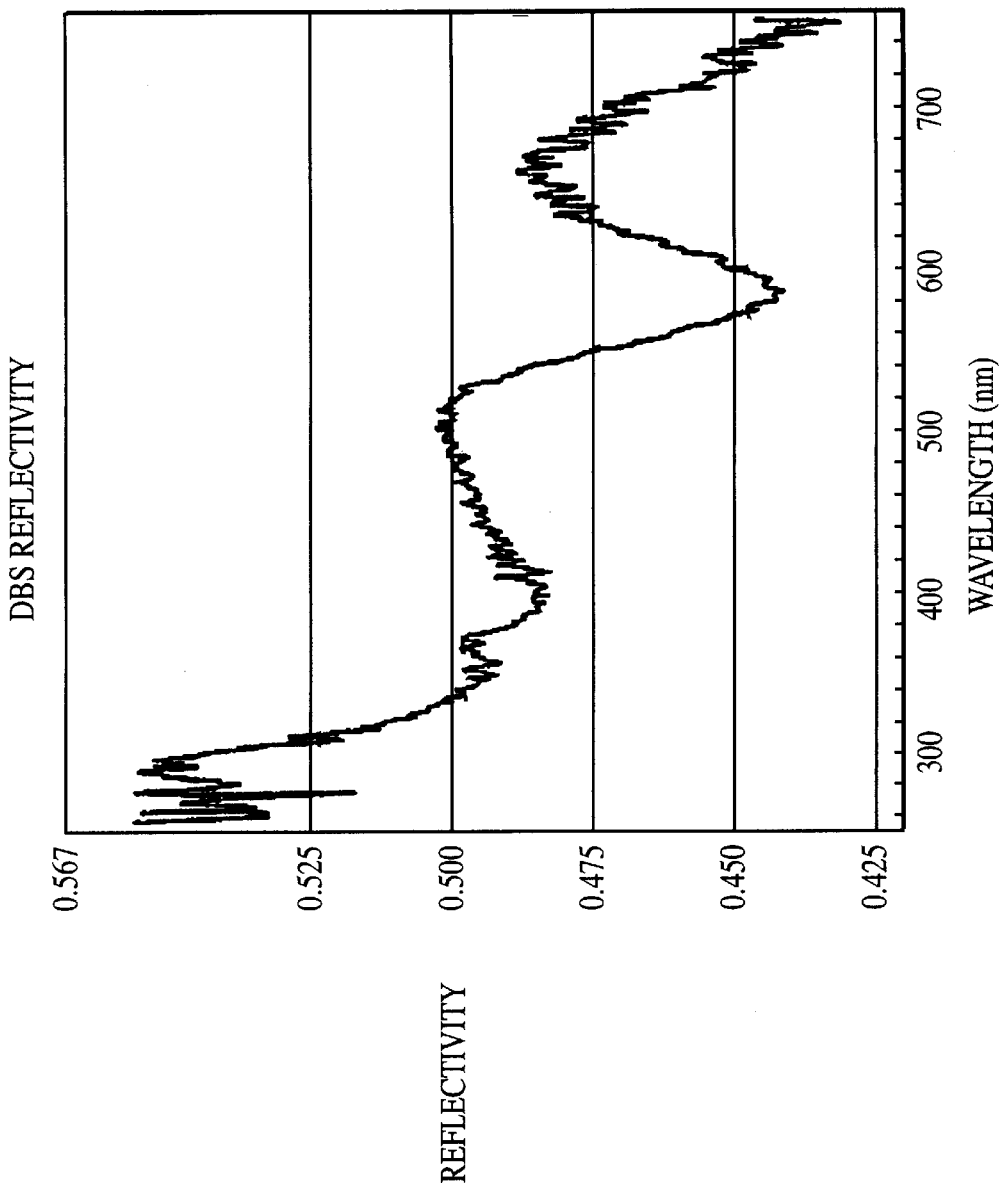
FIG. 9 is a graphical representation of reflectivity versus wavelength for the wafer of FIG. 8 measured in accordance with a preferred embodiment of the present invention.
Figure 10:
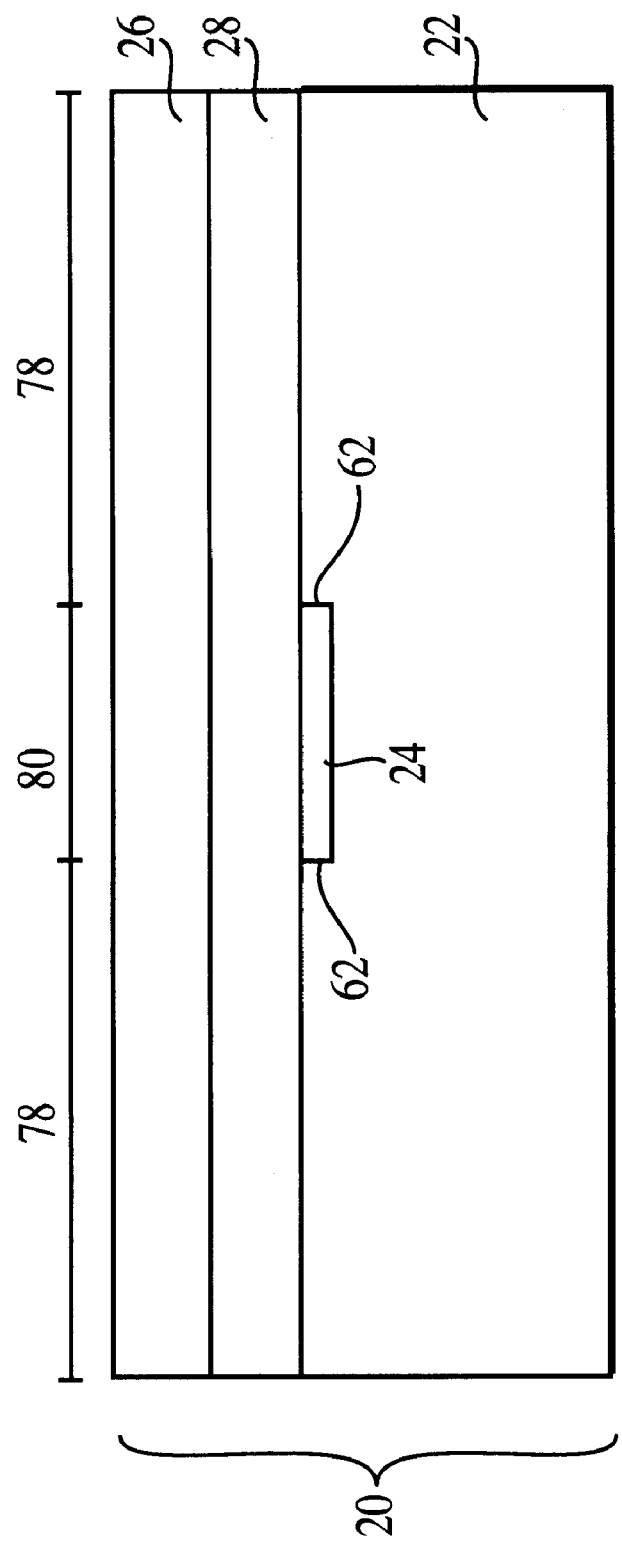
FIG. 10 is a perspective view of a wafer used to illustrate a preferred embodiment of the present invention.
Figure 11:
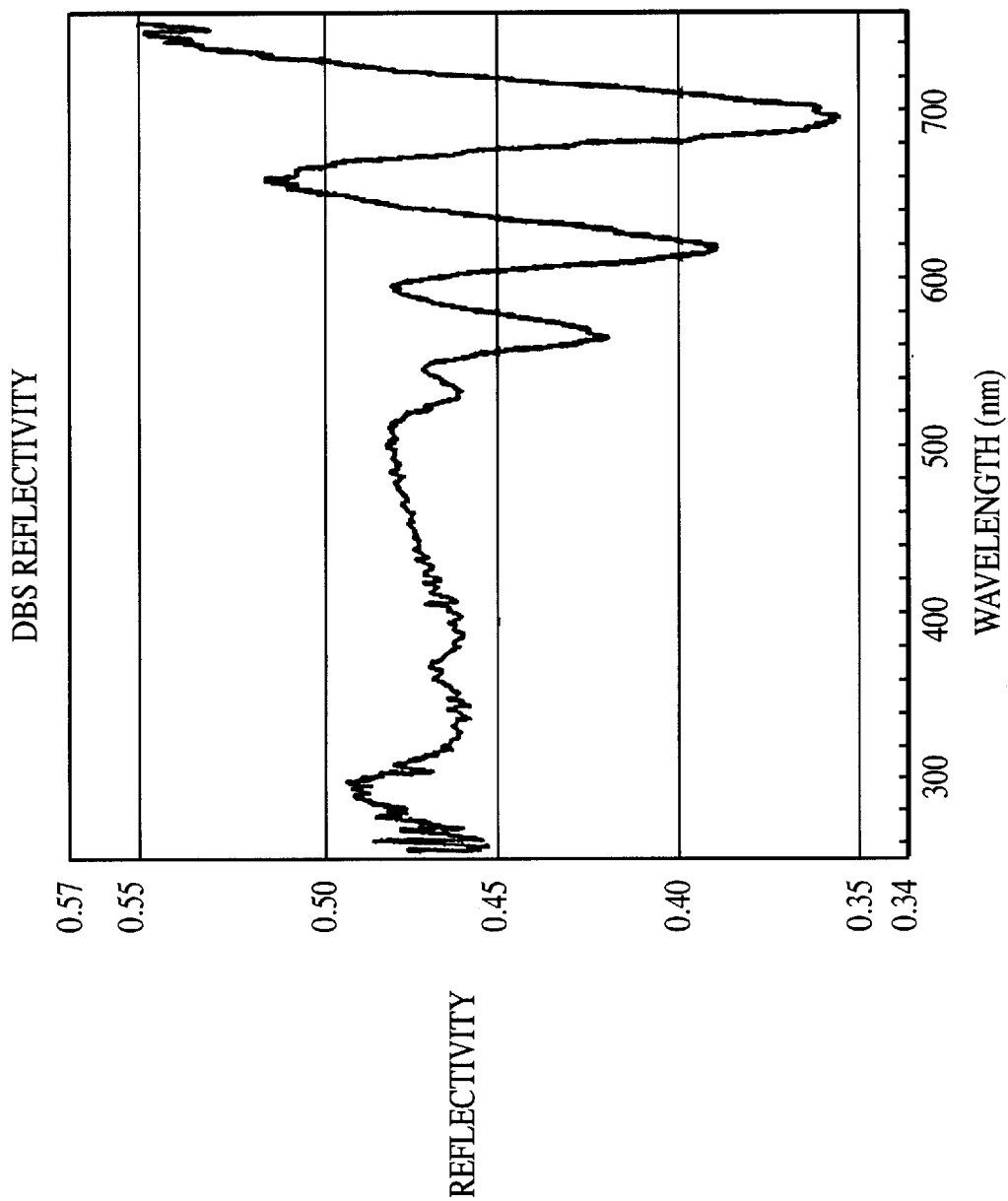
FIG. 11 is a graphical representation of reflectivity versus wavelength for the wafer of FIG. 10 measured in accordance with a preferred embodiment of the present invention.

By way of further example, FIG. 8 shows a wafer 20 comprised of a silicon substrate 22 and a variety of material layers including a silicon oxide layer 24 having a thickness of approximately 90 Angstroms, a polysilicon layer 28 having a thickness of approximately 850 Angstroms, and a Wsix layer 26 having a thickness of approximately 1250 Angstroms. FIG. 9 is a graphical display representing reflectivity versus wavelength of the incident beam 34 and 60 directed at and reflected from section 76 of the wafer 20 of FIG. 8. FIG. 10 shows a wafer 20 comprised of a silicon substrate 22 and a variety of material layers including a silicon oxide layer 24 having a thickness of approximately 1000 Angstroms, a polysilicon layer 28 having a thickness of approximately 4000 Angstroms, and a Wsix layer 26 having a thickness of approximately 1250 Angstroms. FIG. 11 is a graphical display representing reflectivity versus wavelength of the incident beam 34 and 60 directed at and reflected from section 80 of the wafer 20 of FIG. 10. Known data such as that displayed in FIGS. 6, 7, 9, and 11 may be used to compare reflectivity readings from a wafer 20 being measured using the apparatus and methods of the present invention to determine the exact material boundaries or feature edges of regions 76 (FIG. 8) and 80 (FIG. 10).

Returning to FIG. 4, once one or more feature edge 62 have been detected, the controller 42 determines the position of the incident beam 34 relative to the wafer 20 using the coordinate table 36 which monitors the position of the wafer 20 on two or three dimensions. Next, a control element 52 positions the mask 50 over the wafer 20 responsive to positional data from controller 42 in step S222. The positioning of the mask 50 may be accomplished by a human operator through control interface 46 or by the controller 42 in an automated fabrication production line. The wafer 20 may then be subjected to photolithography or other processing techniques requiring correct alignment of a pattern mask in step S224.

The feature edge detection system of the present invention may be implemented at various stages within a semiconductor wafer fabrication production line. The detection system may be used prior to deposition of one or more of the material layers 26, 28, 30 and a plurality of detection systems may be implemented within the same wafer fabrication production line to assist in the identification of feature edges 62 on wafers 20 whenever such identification is requited or desired.

With the present invention, the identification of material layer feature edges 62 in a wafer 20 by a human or machine at any stage of a wafer fabrication process is simplified and does not suffer from the obfuscation which occurs in current optical systems and, therefore, allows for precise and repeatable registration of masks onto wafers 20.

It should be readily understood that the invention is not limited to the specific embodiments described and illustrated above. Rather, the invention can be modified to incorporate any number of variations, alterations, substitutions or equivalent arrangements not heretofore described, which are commensurate with the spirit and scope of the invention. Accordingly, the invention is not limited by the foregoing description, but is only limited by the scope of the appended claims.

What is claimed as new and desired to be protected by Letters Patent of the United States is:

1. An apparatus for the detection of material layer boundaries in a semiconductor wafer, said apparatus comprising:
   an electromagnetic radiation source for emitting an electromagnetic radiation beam directed at a mounting surface for a wafer, said electromagnetic radiation beam having a property that it will be reflected by a material layer of a wafer when the wafer is mounted on said mounting surface;
   an electromagnetic radiation detector positioned to receive a reflected electromagnetic radiation beam and for measuring the intensity of the electromagnetic radiation beam after the electromagnetic radiation beam has been reflected from a material layer of a wafer;
   a system for moving said radiation source and detector relative to said wafer mounting surface such that said electromagnetic radiation beam and associated reflected beam scan an area of a wafer mounted on said mounting surface; and
   a device coupled to said detector for determining a change in intensity of said reflected beam when said radiation beam scans over a boundary region of a material layer of a wafer mounted on said mounting surface.

2. The apparatus of claim 1, wherein said source is part of a reflectometer.

3. The apparatus of claim 1, wherein said detector is part of a reflectometer.

4. The apparatus of claim 1, wherein said source and said detector are contained within a single reflectometer.

5. The apparatus of claim 1, wherein said electromagnetic radiation beam has a range of wavelengths between about 100 nm to about 1000 nm.

6. The apparatus of claim 1, wherein said electromagnetic radiation beam has a spot size has an area of less than about 10 microns in the form of a rectangle.

7. The apparatus of claim 1, wherein said electromagnetic radiation beam has a spot size has an area of less than about 1 micron in the form of a rectangle.

8. The apparatus of claim 4, wherein said reflectometer is positioned relative to said mounting surface such that the electromagnetic radiation is incident said mounting surface at approximately a right angle.

9. The apparatus of claim 4, wherein said system moves said reflectometer along at least a plane of said mounting surface.

10. The apparatus of claim 9, wherein said system also moves said reflectometer in a direction perpendicular to the plane of said mounting surface such that the emitted electromagnetic beam from said reflectometer may be focused on a wafer when mounted on said mounting surface.

11. The apparatus of claim 4, wherein said mounting surface is a platform for holding said wafer.

12. The apparatus of claim 11, wherein said system moves said platform along at least a plane of said mounting surface.

13. The apparatus of claim 11, wherein said system moves said platform in a direction perpendicular to the plane of said mounting surface such that the emitted electromagnetic beam from said reflectometer may be focused on a wafer when mounted on said mounting surface.

14. The apparatus of claim 4, wherein said device includes a display device which displays the intensity of said reflected beam as it moves relative to said mounting surface.

15. The apparatus of claim 4, wherein said device includes a controller which associates a location of said mounting surface relative to said emitting radiation beam when said change in intensity is determined.

16. The apparatus of claim 15, wherein said controller controls the positioning of a processing mask relative to a wafer when mounted on said mounting surface using positional information associated with said change in intensity.

17. The apparatus of claim 15, wherein said controller further comprises a coordinate table connected to said controller and at least one of said mounting surface and said reflectometer for determining the relative positions of at least one of said reflectometer and said mounting surface.

18. The apparatus of claim 15, further comprising an input device coupled to said controller for receiving input from an operator.

19. The apparatus of claim 1, further comprising a wafer mounted on said mounting surface for scanning by said electromagnetic radiation source.

20. A method of identifying a material layer boundary in a semiconductor wafer comprising the steps of:
   emitting an electromagnetic radiation beam directed at a surface of the wafer, said electromagnetic radiation beam being emitted from a reflectometer and having a property that it will be reflected by a material layer of said wafer;

measuring the intensity of the electromagnetic radiation beam with said reflectometer after the electromagnetic radiation beam has been reflected from said layer; and monitoring the measured intensity of the reflected electromagnetic radiation beam for a change in intensity.

21. The method of claim 20, wherein said property of said electromagnetic radiation beam is said electromagnetic radiation beam having wavelengths in the range between about 100 nm to about 1000 nm.

22. The method of claim 20, further comprising the step of positioning said reflectometer relative to said wafer such that the electromagnetic radiation beam is incident said wafer at approximately a right angle.

23. The method of claim 20, further comprising the step of moving at least one of said wafer or said reflectometer such that said step of measuring may be accomplished for different sections of said wafer.

24. The method of claim 23, wherein said step of moving further comprises monitoring the relative positions of said wafer and said reflectometer to a fixed point or each other.

25. The method of claim 20, wherein said step of monitoring further comprises moving said reflectometer along a plane parallel to said surface of said wafer.

26. The method of claim 20, wherein said step of monitoring further comprises focusing said electromagnetic radiation through movement of said reflectometer along a plane perpendicular to said surface of said wafer.

27. The method of claim 26, wherein said electromagnetic radiation beam has a spot size area of less than approximately 10 microns in the form of a rectangle.

28. The method of claim 26, wherein said electromagnetic radiation beam has a spot size area of less than approximately 1 micron in the form of a rectangle.

29. The method of claim 20, further comprising the step of displaying at least one of the results of said step of measuring and said step of monitoring using a graphical representation.

30. The method of claim 20, further comprising the step of incorporating said reflectometer into a production line of said wafer.

31. The method of claim 30, wherein said step of incorporating is accomplished by locating said reflectometer within said production line before an area where said wafer is subjected to photolithography.

* * * * *